(12) United States Patent
Moore et al.

(10) Patent No.: US 6,777,674 B2
(45) Date of Patent: Aug. 17, 2004

(54) METHOD FOR MANIPULATING MICROSCOPIC PARTICLES AND ANALYZING

(75) Inventors: Thomas M. Moore, Dallas, TX (US); John M. Anthony, Austin, TX (US)

(73) Assignee: Omniprobe, Inc., Dallas, TX (US)

( * ) Notice: Subject to any disclaimer, the term of this patent is extended or adjusted under 35 U.S.C. 154(b) by 0 days.

(21) Appl. No.: 10/252,659

(22) Filed: Sep. 23, 2002

(65) Prior Publication Data

US 2004/0056194 A1 Mar. 25, 2004

(51) Int. Cl.[7] ............................ G01N 23/22; G01N 1/28
(52) U.S. Cl. .................................... 250/307; 250/442.11
(58) Field of Search ............................ 250/307, 442.11, 250/311, 440.11, 288; 73/864, 81, 86

(56) References Cited

U.S. PATENT DOCUMENTS

| | | | | |
|---|---|---|---|---|
| 4,590,792 | A | * 5/1986 | Chiang | ...................... 73/28.06 |
| 5,584,938 | A | 12/1996 | Douglas | ...................... 134/1.3 |
| 5,858,108 | A | 1/1999 | Hwang | ....................... 134/1.3 |
| 6,184,686 | B1 | 2/2001 | Mazor et al. | ................ 324/464 |
| 6,188,068 | B1 | * 2/2001 | Shaapur et al. | .............. 250/307 |
| 6,256,825 | B1 | 7/2001 | Hwang | ....................... 15/1.51 |
| 6,362,475 | B1 | 3/2002 | Bindell et al. | ............... 250/307 |
| 6,538,254 | B1 | * 3/2003 | Tomimatsu et al. | .... 250/442.11 |

FOREIGN PATENT DOCUMENTS

WO 028065 4/2003

OTHER PUBLICATIONS

Mikihiko Kobayashi, Hiroshi Fudouzi, Mitsuru Egashira, Norio Shinya, "Particle arrangement and its application", Materials and Design 21 (2000) 571–574, 5th Research Group, National Research Institute for Metals, 1–2–1 Sengen, Tsukuba, Ibaraki 305–0047, Japan.

T. Konno, M. Egashira, M. Kobayashi and N. Shinya, "Micro welding method using a tungsten probe for micro fabrication", National Research Institute for Metals, 1–2–1, Sengen, Tsukuba, Ibaraki 305–0047, Japan.

Hideki T. Miyazaki, Yasushi Tomizawa, Shigeki Saito, Tomomasa Sato, Norio Shinya, Adhesion of micrometer–sized polymer particles under a scanning electron microscope; 2000 American Institute of Physics, vol. 88, No. 6, Sep. 15, 2000.

Hideki Miyazaki, Yasushi Tomizawa, Koichi Koyano, Tomomasa Sato, Adhesive forces acting on micro objects in manipulation under SEM; Research Center for Advanced Science and Technology, The University of Tokyo, 4–6–1 Komaba, Meguro–ku, 153 Tokyo, Japan, Hitachi Ltd., 1 Horiyamashita, Hadano, 259–13 Kanagawa, Japan, pp. 197–208, vol. 3202.

Hideki T. Miyazaki, Yasushi Tomizawa, Shigeki Saito, Tomomasa Sato, Norio Shinya, Adhesion force measurement system for micro–objects in a scanning electron microscope, 2000 American Institute of Physics, vol. 71, No. 8, Aug. 2000.

N. Shinya, T. Konno, M. Egashira, "Micro–scale structure fabrication using micro–probe", National Research Institute for Metals, 1–2–1, Sengen, Tsukuba, Ibaraki 305, Japan.

* cited by examiner

Primary Examiner—John R. Lee
Assistant Examiner—James J. Leybourne
(74) Attorney, Agent, or Firm—John A. Thomas

(57) ABSTRACT

We disclose a method for analyzing the composition of a microscopic particle resting on a first sample surface. The method comprises positioning a micro-manipulator probe near the particle; attaching the particle to the probe; moving the probe and the attached particle away from the first sample surface; positioning the particle on a second sample surface; and, analyzing the composition of the particle on the second sample surface by energy-dispersive X-ray analysis or detection of Auger electrons. The second surface has a reduced or non-interfering background signal during analysis relative to the background signal of the first surface. We also disclose methods for adjusting the electrostatic forces and DC potentials between the probe, the particle, and the sample surfaces to effect removal of the particle, and its transfer and relocation to the second sample surface.

65 Claims, 5 Drawing Sheets

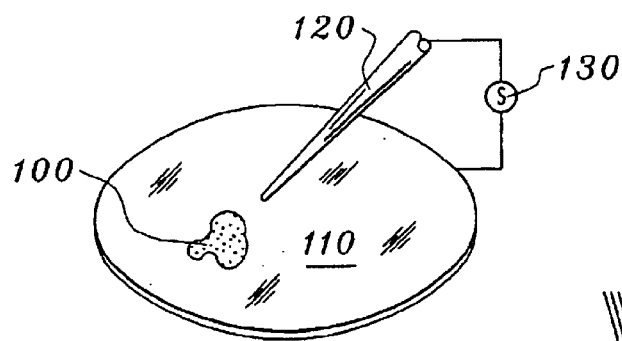
Fig. 1-A
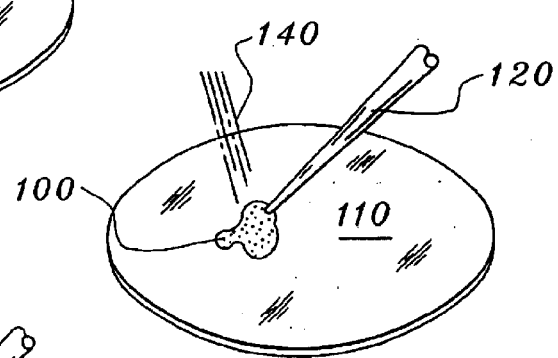
Fig. 1-B
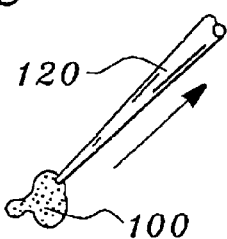
Fig. 1-C
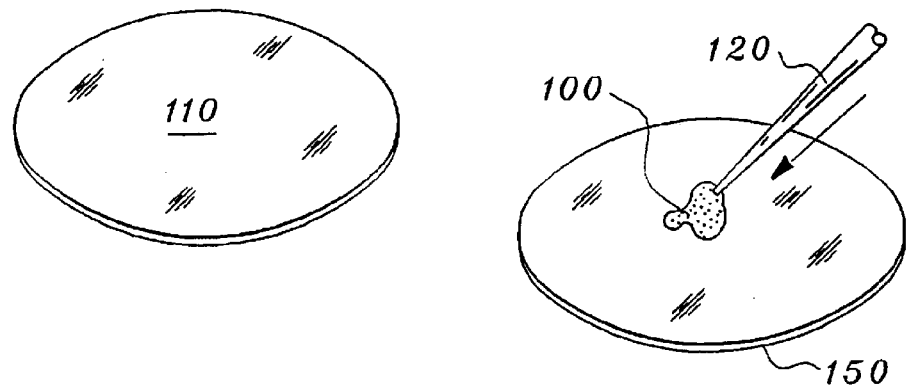
Fig. 1-D

*Fig. 2-A*
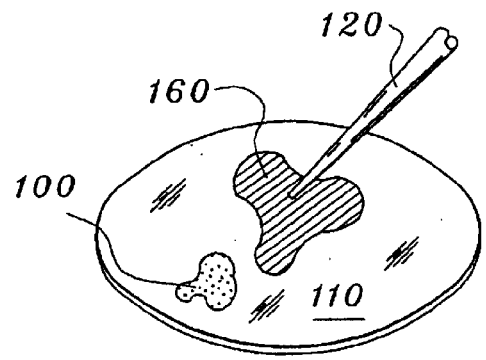
*Fig. 2-B*
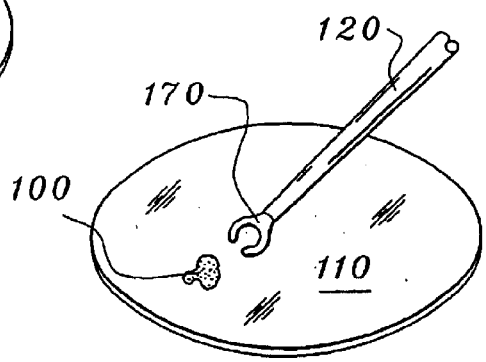
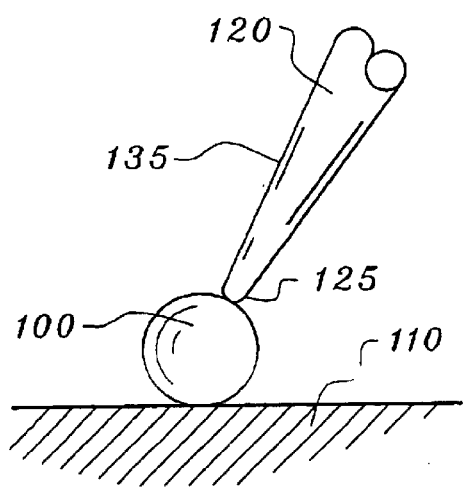
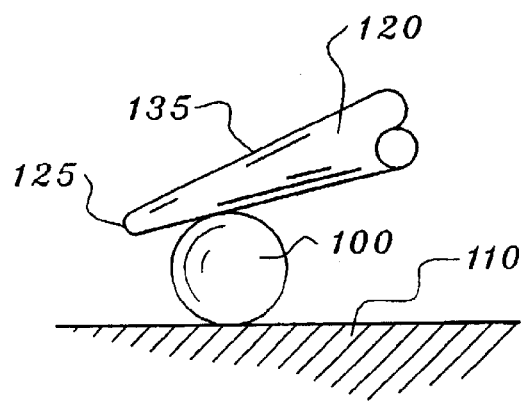
*Fig. 2-C*         *Fig. 2-D*

Fig. 3-A
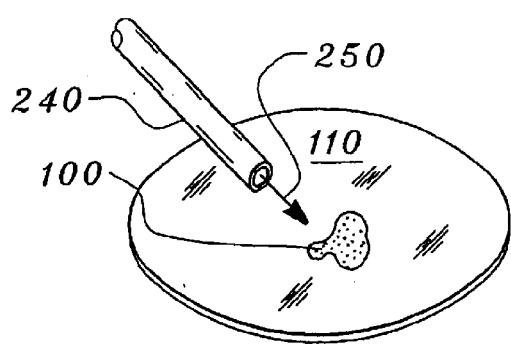
Fig. 3-B
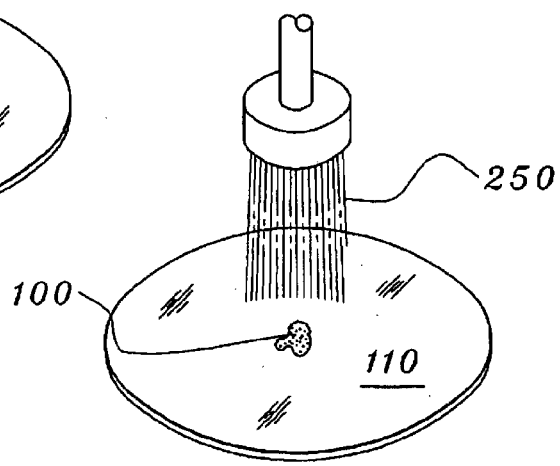
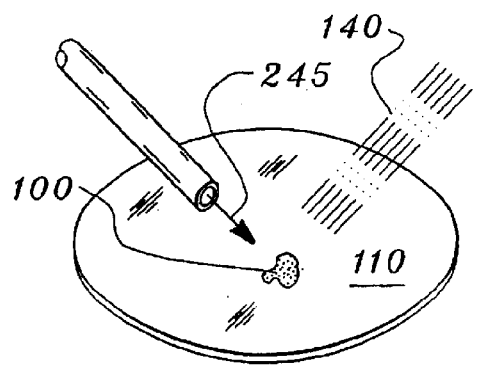
Fig. 3-C
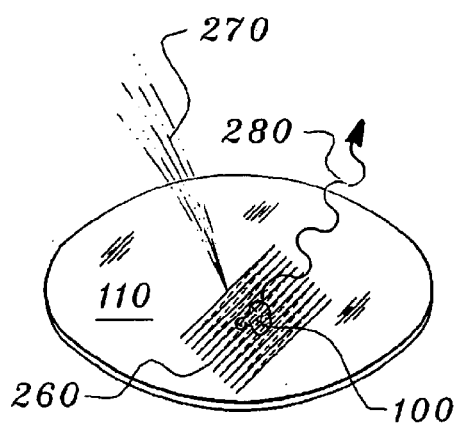
Fig. 4

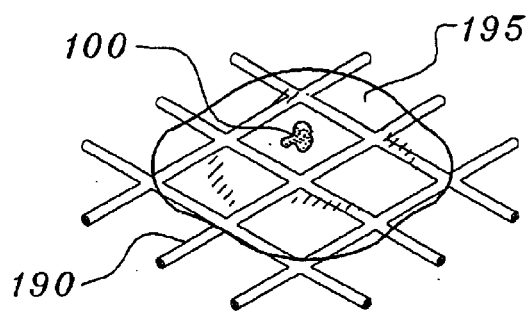
Fig. 5-A
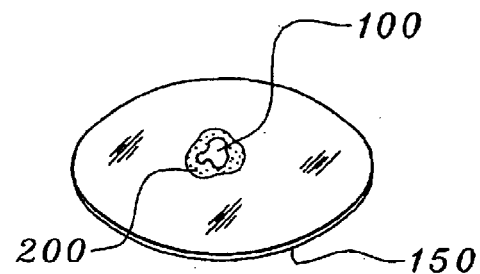
Fig. 5-B
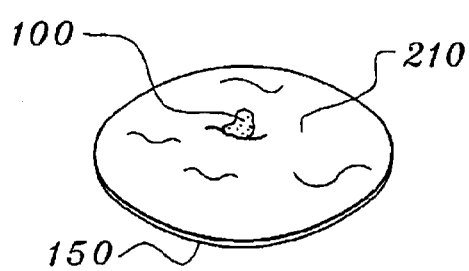
Fig. 5-C
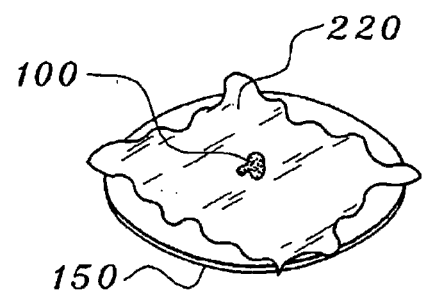
Fig. 5-D
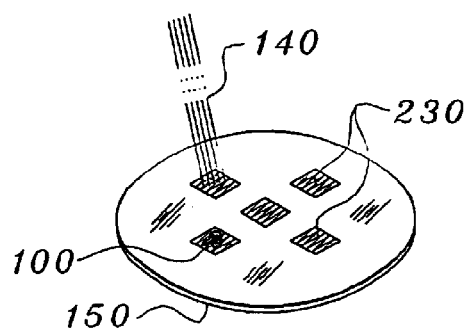
Fig. 5-E
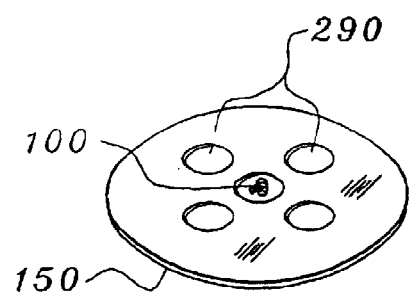
Fig. 5-F

METHOD FOR MANIPULATING MICROSCOPIC PARTICLES AND ANALYZING

FIELD OF THE INVENTION

The invention relates to techniques for removing and analyzing microscopic particles from a sample surface, particularly from semiconductor samples.

BACKGROUND

In the semiconductor industry, unexpected particles due to contamination will cause yield loss during the manufacturing process. Since a major focus of this industry is aggressive reduction in feature size for pattern line widths, the minimum size of particles that can cause performance loss also decreases rapidly. A reasonable estimate for a "killer defect" size is that greater than one-third the size of the smallest feature on the semiconductor wafer.

Although semiconductor manufacturing is performed in clean rooms with stringent particle standards, unexpected contamination will occur due to sources such as moving parts, human presence, gas condensation, and chamber wear. Control and removal of these particles is a continuous process. In many cases, removal of the source of particles requires an understanding of their origin. Many of these particles or defects are too small for detection in a general purpose optical inspection microscope, so higher resolution methods are required, using charged-particle microscopes, such as scanning electron microscopes (SEM), transmission electron microscopes (TEM), scanning Auger microprobes (SAM), or focused ion beam (FIB) instruments, are required.

Even an image of the particle is usually insufficient to trace the origin of the particle, and more information is required. Elemental composition is valuable in identifying the defect. This can be done in various ways using the charged-particle systems mentioned above. Unfortunately, most of the analytical methods are limited by background signals from the environment of the particle.

Throughput is also a critical parameter in semiconductor manufacturing. Existing strategies for compositional analysis of particles on a semiconductor wafer, for example, usually require removal of the wafer from the fabrication area for off-line analysis using methods such as those described below. Removal from the line severely reduces the throughput of the manufacturing process.

Particle identification on sample surfaces using electron-beam based identification is complicated by the size of the particle relative to the electron penetration depth, and by the nature of surrounding materials in the sample. As an electron beam interacts with bulk solid materials, it expands to fill a teardrop-shaped volume as it loses energy. As the primary beam interacts with atoms in this volume, it generates low energy Auger electrons and X-rays that are characteristic of the elements involved.

The particular X-ray line generated will depend on the atomic number of the element, the energy of the electron during the interaction, and other factors. When trying to identify an unknown particle using conventional Energy-dispersive X-ray Spectrophotometry (EDS), the energy of the electron beam must be large enough to generate inner-shell X-rays from all possible relevant elements, which, for semiconductor applications, may include elements of high atomic number such as tungsten. Unfortunately, this energy results in a penetration depth that may be much larger than the particle of interest, resulting in X-ray generation from the sample surface. These X-rays interfere with any signal from the particle, making unique identification of the particle material difficult. Conventional strategies for solving this problem involve either resolving the X-ray lines of different elements, or reducing the energy of the exciting electron beam.

For example, it is possible to detect and analyze electron-beam generated X-rays from a particle by measuring the intensity and diffraction angle of the X-rays diffracted by a reference crystal, or Wavelength Dispersive X-ray Spectrometry (WDS). One chooses the crystal atomic spacing to deflect (with very high resolution) X-rays of a given energy, thus allowing separation between X-ray lines of different elements. This method has higher energy resolution than EDS but much slower throughput. In addition, if the particle could be, as it often is, of the same composition as the sample surface, this method will not uniquely determine the particle composition.

Other solutions involve reducing the energy of the primary electron beam to guarantee the activated volume is less than the volume of the particle of interest. This reduction in primary electron-beam energy results in characteristic X-rays of much lower energy (M or L shell X-rays, rather than K shell). Conventional cooled semiconductor-based detectors use the generation and collection of electron-hole pairs as a measure of the energy of the ionizing radiation (a few eV for each electron-hole pair, depending on the detecting material). A reduction in the X-ray energy therefore leads to a reduced number of electron-hole pairs and reduced sensitivity to the particle material. In addition the resolution of these detectors is governed by the statistics of the electron-hole generation process, and reducing the energy of the detected X-ray often leads to ambiguous identification of the element of interest. X-ray micro-calorimeter methods have been used to detect these weak X-ray signals, using heat transferred to the detector rather than the generation of electron-hole pairs. This process does allow measurement of small X-ray energies, but micro-calorimeter instruments are expensive, have complicated cooling requirements, and are slow compared to other methods. Also, the electron beam must be kept smaller than the smallest dimension of the particle of interest, rendering the method impractical for small, unsymmetrical particles.

Scanning Auger microprobe analysis also uses an electron beam to irradiate a particle of interest, but rather than detecting any X-rays generated it focuses on the detection of Auger electrons ejected from the atoms of the material. These Auger electrons come from outer shells and have relatively low energies. The Auger electron energies from a material produce a pattern that is characteristic of each element in the material, and the shape and exact energy of the Auger transitions provide information on the chemical bonding of the elements in the material (such as, phase or compound information). The escape depth of these electrons is quite small (a few nm), so Auger analysis focuses mainly on the surface of a sample. This is an advantage for the analysis of small diameter particles (<10 nm). For the analysis of larger particles, one can generate depth profiles by using an ion beam to sputter through the particle and take periodic measurements, but this is inherently destructive of the surrounding sample due to ion milling in the SAM, and requires background analyses on the sample near the location of the particle. Auger analysis is typically more sensitive to light elements than standard EDS analysis, making it more suitable to identify organic materials. However, to improve counting statistics, high electron beam currents are typically employed. This exaggerates the issues of thermo-mechanical drift and drift due to electrical charging of the sample. This means that operating the SAM in the "spot mode," with the electron beam positioned on the particle, involves a risk that over time the electron beam spot will drift onto the sample that surrounds the particle. And the use of a raster pattern for the electron beam will be more tolerant of drift for keeping the beam on the particle, but will involve significant contamination of the results with signal from the surrounding material. In either case, background contamination of the Auger results is a serious issue, and Auger analyses of the surrounding material are required to uniquely identify the signal from the particle. The acquisition of background analyses reduces throughput and inherently damages the sample.

TEM can often be used for analysis of particles in or on surfaces. There are a variety of methods for isolating the particle for analysis, including replication, lift-out or cross sectioning the area of interest. These methods all destroy the sample surface and must be done off-line, thereby increasing cost and cycle time.

Moving the particle from the first sample surface to a more controlled environment for testing can dramatically improve the chance of success and throughput for elemental identification with either EDS or Auger analysis. A critical part of this process is the strategy for moving the particle. This disclosure describes a novel method for removing a particle of interest from a sample surface, transporting that particle to a second sample surface with a controlled X-ray or Auger background, and performing electron beam-induced X-ray analysis or Auger electron analysis there, using any of the methods discussed above. This eliminates the requirement that the analyzing technique have high spatial resolution, although a technique with high spatial resolution, such as EDS analysis in the SEM and SAM analysis, is generally preferred. For example, techniques without high spatial resolution that could be successfully applied to the situation of a particle on a reduced or non-interfering background include X-ray Photoelectron Spectroscopy (XPS) and X-ray Fluorescence analysis (XRF), which may offer an advantage in unique and specific situations.

The proposed method for particle manipulation and EDS X-ray analysis can be done in-line on existing wafer-manufacturing tools. An in-line procedure using existing manufacturing and inspection tools represents a significant reduction in cycle time for contamination removal. SEM is a routine method for wafer inspection, and analytical methods using the electron beam in an SEM system provide a substantial throughput advantage over the off-line strategies.

Although this disclosure primarily illustrates the use of the novel technique to manipulate and examine particles that are contaminants in the context of semiconductor manufacturing, the reader should note that the term "particle" may be taken to include objects that may not be contaminants in other environments, such as chemical deposits, biological material, or micro-mechanical machines. In the latter cases, the novel methods of manipulation described in this application may be applied to manipulate these objects generally, for purposes other than electron-beam X-ray analysis or Auger electron analysis.

FIGURES

FIG. 1 shows the steps of attaching a particle to a micro-manipulator probe and removing the particle to a second surface for analysis.

FIG. 2 shows three other methods of attaching a particle to a micro-manipulator probe.

FIG. 3 shows the process of modifying electrostatic forces by bombardment with polarizable molecules.

FIG. 4 shows the method of simultaneously viewing a particle and modifying the charge state of the particle.

FIG. 5 shows several methods for fixing a particle to a second surface for analysis.

SUMMARY

Figure 6:
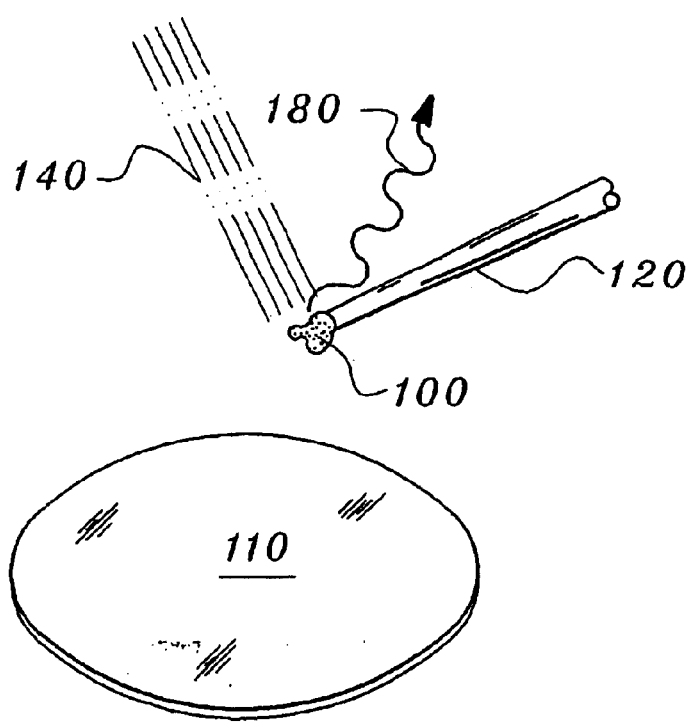
FIG. 6 shows the analysis of a particle while the particle is fixed to the tip of a micro-manipulator probe.

We disclose a method for analyzing the composition of a microscopic particle resting on a first sample surface. Usually, the particle will be a contaminant in a semiconductor processing system, although the method is not limited to those circumstances. The method comprises positioning a micro-manipulator probe near the particle; attaching the particle to the probe; moving the probe and the attached particle away from the first sample surface; positioning the particle on a second sample surface; and, analyzing the composition of the particle on the second sample surface by energy-dispersive X-ray analysis, Auger microprobe analysis or any other suitable analytical technique. The second surface has a reduced or non-interfering background signal during analysis, relative to the background signal of the first surface. (We call such a reduced or non-interfering background signal a "controlled" background signal in the claims.) We also disclose methods for adjusting the electrostatic forces and DC potentials between the probe, the particle, and the sample surfaces to effect removal of the particle, and its transfer and relocation to the second sample surface. These include adjusting electrostatic forces to create an attractive force between the probe and particle. Adjustment of the electrostatic forces may include locally adjusting the energy or intensity (intensity means beam current for electron and ion beams) of an electron beam, ion beam or photon beam incident on the individual components of the sample system, which includes the probe tip, particle and first sample surface, to create an electrostatic attraction between the particle and probe tip, or an electrostatic repulsion between the particle and the first sample surface. This procedure is reversed to transfer the particle from the probe tip to the second sample surface.

The second sample surface may be the probe tip itself. In this case the probe tip is composed of a controlled background material. Due to the possibility of transmission of the energetic beam through a tiny particle, or scattering of the energetic beam onto the underlying surface, it may be necessary to translate the probe tip with the particle attached over a surface composed of a controlled background material, or alternatively translate such a controlled background surface beneath the probe tip with the particle attached. In this description, "under" and "beneath" refer to the side of the particle opposite the side on which the energetic beam is incident (i.e.: the transmitted side).

DETAILED DESCRIPTION

The analysis of microscopic particles, particularly in semiconductor manufacturing, is typically done inside a Scanning Electron Microscope (SEM), Focused Ion Beam (FIB) instrument, or Scanning Auger Microprobe (SAM). The FIB instrument may be either a single-beam model, or a dual-beam (both SEM and ion beam) model. Typical FIB instruments are those manufactured by FEI Company of Hillsboro, Oreg., as models 200, 235, 820, 830, or 835. The probe (120) referred to below is a component of a micro-manipulator tool attached to the FIB instrument with vacuum feed-through. A typical such micro-manipulator tool is the Model 100 manufactured by Omniprobe, Inc. of Dallas, Tex. Typical SAM instruments include the JAMP-7810 and JAMP-7830F manufactured by JEOL USA, Inc. of Peabody, Mass.

FIG. 1 depicts the general setup for particle manipulation and analysis. FIG. 1A shows a particle (100) of interest resting on a first sample surface (110). A micro-manipulator probe (120) is positioned near the particle (100). The probe tip can be electrostatically charged relative to the particle and the first sample surface. Alternatively, a voltage source (130) may be connected between the probe (120) and the first sample surface (110). The local electrostatic charge on the particle can be modified by the irradiation of the particle by a charged particle beam. FIGS. 1B through 1D show, respectively, the irradiation of the particle (100) and first sample surface (110) by photons or a charged-particle beam (140) to cause attachment of the particle (100) to the probe (120), the removal of the probe (120) and attached particle (100) from the first sample surface (110), and the deposition of the particle (100) on a second sample surface (150) for analysis. The drawings are not to scale.

Attaching the Particle to the Probe

Strong electrostatic forces exist on particles in a vacuum. The presence of static charges on the particle (100) and the probe (120) leads to the creation of image charges on the opposite surfaces. These image charges create forces that are proportional to the area exposed and inversely proportional to the distance between the objects. Reducing or increasing the exposed area will therefore either reduce or increase the force acting on the particle (100), and the resultant adhesion between probe (120) and particle (100). This can be used as a straightforward method to remove particles of interest from the sample, using either a conducting or insulating probe (120). Conducting probes allow more versatility through the introduction of static or time varying voltages or electrostatic charges to the probe (120) from a voltage or electrostatic charge source (130), as shown generally in FIG. 1A.

The shape of the tip of the probe (120) will also influence the electric fields at the tip. Static electric charges on a blunt tip will exert stronger influence on a particle in line with the tip than a sharply pointed tip. In contrast, in the case of a DC potential on a conductive tip, a sharp tip will produce the strongest field concentration at the tip. The probe (120) can be moved into proximity to the particle (100) while imaging with, for example, the electron beam (140) available in the FIB instrument, as shown in FIG. 1B. The electron beam will also affect the charge distribution in the surface-particle-probe system, and thus can assist attraction of the particle (100) to the probe (120). An application of this effect is discussed below. The electron beam (140) depicted in FIG. 1B and other drawings should be understood to also be a charged-particle beam or photon beam generally, and may, for example, consist of an ion beam. These, and beams of photons, such as from a laser, are referred to collectively in the claims as "energetic" beams.

In general, the adjustment of electrostatic forces on the system may comprise adjusting the energy of an electron beam (140) incident on the particle (100), probe (120), and first sample surface (110) to create a relative electrostatic attraction between the particle (100) and the probe (120), and a relative electrostatic repulsion between the particle (100) and the first sample surface (110). The process may be assisted by a voltage source (130) connected between the first sample surface (110) and the probe (120). Clearly, the impinging beam (140) could also be a beam of photons, having sufficient energy to release photoelectrons, which thus change the charge distribution in the system, and the electrostatic forces involved.

The preferred embodiment may also be carried out using an adhesive (160) on the probe (120), as shown in FIG. 2A. An acceptable adhesive (160) could be any having a low vapor pressure, such as vacuum grease, low melting point waxes, or other low vapor pressure glues. In this case, the forces of adhesion simply capture the particle (100), notwithstanding existing electrostatic forces.

In another embodiment, shown in FIG. 2B, tweezers (170) connected to the probe (120) grasp the particle (100) and remove it from the first sample surface (110). Suitable device having tweezers (170) or similar grippers are those manufactured by MEMS Precision Instruments in Berkeley, Calif.

The probe (120) can touch the particle (100), but this is not necessary in many cases, as the particle (100) will jump to the probe (120) due to the electrostatic attraction. The electrostatic field is controlled by surface area and therefore enhanced with a blunt tip on the probe (120), or the blunt side of a particle (100) or the probe (120), whereas DC potentials are enhanced by a pointed tip that concentrates the field lines. FIGS. 2C and 2D show examples of strategies for particle (100) attachment and transfer by controlling the surface area of the particle (100) exposed to the manipulator, by applying the tip (125) of the probe (120) and the side (135) of the probe (120) to the particle to achieve the desired movement of the particle (100).

An additional method of adjusting the electrostatic fields in the particle-probe-surface system, for both attaching and removing the particle (100) comprises depositing a conductive material on the first sample surface (110) or second sample surface (150), as the case may be, to distribute and modify the electrostatic charge on the surface at the location of the particle to create either an attractive or a repulsive force on the particle, as desired. FIG. 3A depicts the deposit of polarizable molecules (250), such as water, on the sample surface (110). FIG. 3B depicts the deposit of a conductive film (255) by evaporation of a source. FIG. 3C depicts a directed jet (240) of gas (245) applied to a surface (110) having a particle (100) resting upon the surface (110). The gas (245) is decomposed by an energetic beam (140), which may be an electron beam, an ion beam, or photons, such as from a laser.

A method of simultaneously viewing a particle (100) in a vacuum system and adjusting the charge state of the particle is shown in FIG. 4. The SEM beam and the ion beam in typical FIB instruments are scanned over the object of interest in a raster pattern (260). This scanning, synchronized with emitted secondary electrons, generates the electrical signal that is displayed as an image to the operator of the instrument. Since the scanning beam necessarily comprises charged particles, and causes charged particles, such as secondary electrons, to be emitted from the sample, it may itself be used to change the charge state of the particle (100). FIB instruments typically use digital scan generators that digitally increment the position of the beam spot through a raster pattern, one line at a time, often reversing direction between lines to eliminate the flyback after each line that characterizes traditional analog scanners. So the operator, or the computer program controlling the scan, can determine the dwell time on a per-pixel basis. For example, a box covering the particle (or the exact outline shape of the particle) can be programmed with zero dwell time, and therefore blanked during the scan. Any dwell time can be set up to the maximum time allowed by the line rate to avoid image distortion in a single scan. It is also possible to alternately scan around the box, and then scan in the box with different parameters, and do this so quickly that the human eye would not see an interruption.

FIG. 4 shows the steps of rastering a primary electron beam (270) over a field of view that includes the particle (100); generating and detecting secondary electrons (280) that are synchronized with the primary beam (270); and modifying the raster scan pattern (260) to specify dwell time and location for specific pixels in the field of the raster (260) associated with the particle (100) to be incorporated and added to the standard raster pattern. The particle (100) then experiences an excess or a reduction of negative charge relative to the sample surface (150) under the rest of the raster (260). Thus the electrostatic field between the particle (100) and the probe (120) and sample surface (150) can be adjusted to achieve attraction or repulsion, as desired. The raster may be generated by ion beams as well, and in the same fashion, by a scanning laser.

Transferring the Particle

Once the particle (100) is attached to the probe (120) by any of the means just described, the probe (120) can be moved within the vacuum environment either manually or via automated probe (120) hardware. An alternative method would be to raise or retract the probe (120) slightly and move the sample stage to bring a controlled background material under the probe (120).

The particle (100) can also be transferred by the probe (120) to the second sample surface (150) consisting substantially of a controlled background material having a low background or non-interfering background signal. For analysis by EDS, low atomic-number materials such as carbon or beryllium produce low-energy X-rays that will not interfere with most non-organic particle-analysis processes. An atomic number less than or equal to 12 is preferred. Organic particles will obviously require a non-organic background material. Examples of the low-background materials for the second sample surface (150) include photoresist, carbon planchette, beryllium foil, conductive carbon-based paste (colloidal graphite suspensions), polymer membranes, or carbon nanotube needles. Any material whose X-ray background does not interfere with the typical materials in the fabrication process may be acceptable for the second sample surface (150). In some cases, the second sample surface (150) may be a different part of the first sample surface (110). In other cases, where the composition of the particle (100) is partly known or suspected, the material of the second sample surface (150) should have a background signal different that the signals expected from the particle (100). Care must be taken that the choice of the second sample surface (150) does not obscure possible signals from contaminants from outside the fabrication facility, such as impurities in incoming gases or chemicals. For Auger analysis of the particle on the second surface, the second surface should consist of low Auger electron background or non-interfering Auger electron background. The composition of the second surface should be consistent to a depth greater than that of any depth profiling that will be performed on the particle. It will be helpful, but not necessary for the second surface material to be electrically and thermally conductive to minimize any charging or thermo-mechanical drift problems associated with high incident electron beam currents. A pre-sputtering of the second surface, before transfer of the particle will remove any native surface coating (mostly carbon and oxygen) and simplify the analysis. This pre-sputtering can be performed, for example, with the depth profiling ion source in the Auger, or the ion beam in the FIB. That the composition of the second surface is well known eliminates the need to acquire background analyses which improves throughput.

FIG. 5 shows several methods for transferring the attached particle (100) from the probe (120) to the second sample surface (150) for the analysis. FIG. 5A shows the particle suspended on an underlying framework (190), thin relative to the penetration depth of the analysis beam (140). The framework (190) would typically be a TEM grid, possibly having a polymer membrane (195) such as FORM-VAR across the grid openings.

FIG. 5B shows the particle attached to the second sample surface (150) by an adhesive (200) on the second sample surface (150). FIG. 5C shows a second sample surface (150) comprising a background material (210) having a low modulus of elasticity, such as vacuum grease, low-melting point wax, or low-modulus polymer. In this case the particle (100) can be pushed into the low-modulus material (210) and stuck there.

FIG. 5D shows a wrinkled surface (220) on an insulating second sample surface (150). The wrinkled surface (220) allows an increased area of contact between the particle (100) and the second sample surface (150), thus changing the electrostatic forces between them.

FIG. 5E shows an electrified pattern (230) written on the second sample surface (150) by the charged-particle beam (140). The electrostatic field of such a pattern can assist in the transfer of the particle from the probe (120) to the second sample surface (150).

FIG. 5F shows a porous second sample surface (150) having holes or pores (290). Such surfaces may be micropore filters, such as the MICROPORE series of filters manufactured by 3M Corporation of St. Paul, Minn., glass fiber filters such as the FILTRETE or EMPORE series of filters manufactured by 3M Corporation of St. Paul, Minn., or "holey carbon" films, such as the QUANTIFOIL series manufactured by Structure Probe, Inc. of West Chester, Pa. These surfaces have the advantage that particles (100) will rest or be electrostatically captured in the holes or pores and be held there for analysis.

In some cases it may be necessary to search for areas of high local static fields sufficient to remove the particle (100) from the probe (120) without contact (if that is desired).

Of course, the methods described in the previous section for adjusting the electrostatic forces in the particle-probe-sample surface system for attaching the particle (100) to the probe (120) can also be used to remove the particle (100) from the probe (120) and attach it to the second sample surface (150). In particular, the voltage or charge source (130) may generate a rapid transient or resonant phenomenon, for example, by rapidly switching stored negative charge from a capacitor through the probe (120), or by a time-varying voltage, such as a square wave or pulse, applied to the probe (120) from the source (130).

Analyzing the Particle

X-ray analysis or Auger analysis can be performed with the particle (100) directly on the probe tip (125), as shown in FIG. 6. This will of course result in X-ray or Auger electron generation from the probe tip (120) itself. Other interfering signals can be reduced by either using a low-background or non-interfering background material for the probe tip material, as discussed above, placing a low-background or non-interfering background material under the probe (120) during this analysis, or by dropping the stage and all other hardware from near the probe (120). Removal of the particle (100) after this step can be performed destructively since the particle (100) analysis has already been done. Example destructive methods might include inserting the probe (120) in a plasma cleaner of some kind, rubbing the particle (100) off on a mechanical transfer structure such as a V-groove, irradiating the probe optically either in vacuum or after exposure to the atmosphere, or ablating the particle (100).

Figure 7:
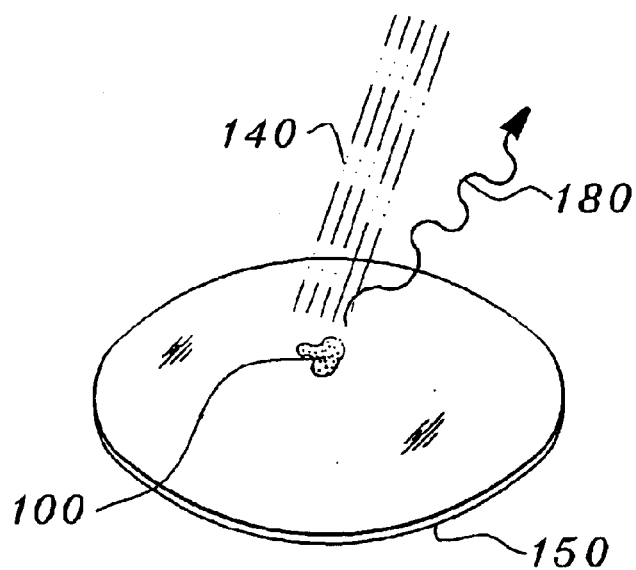
FIG. 7 shows the process of analyzing the composition of a particle removed to a second surface for analysis.

Usually, however, the particle (100) will be analyzed on a second sample surface (150), as depicted generally in FIG. 7, where the particle (100) is irradiated with a charged-particle analysis beam (140), causing it to emit characteristic Auger electrons or X-rays (180) for compositional analysis, by any of the methods described in the Background section of this application. In the claims, the term "emissions" denotes either Auger electrons or X-rays.

Analyzing the Particle on the Probe Tip

The second sample (150) surface may be the probe tip (135) itself. In this case the probe tip (135) is composed of a controlled background material. In the case of a analysis instrument such as SAM or FIB in which ion beam milling of the surface is possible, the surface of the probe tip (135) can be ion milled prior to attachment of the particle (100) to the tip (135) to reduce signals from the native surface coating and debris on the probe tip (135) surface. Due to the possibility of transmission of the energetic beam (140) through a tiny particle, or scattering of the energetic beam (140) onto the underlying surface, it may be necessary to translate the probe tip (135) with the particle (100) attached over a surface composed of a controlled background material, or alternatively translate such a controlled background surface beneath the probe tip (135) with the particle (100) attached. In this description, "under" and "beneath" refer to the side of the particle (100) opposite the side on which the energetic beam (140) is incident (i.e.: the transmitted side).

Since those skilled in the art can modify the specific embodiments described above, we intend that the claims be interpreted to cover such modifications and equivalents.

We claim:

1. A method for analyzing the composition of a particle; the particle resting on a first sample surface; the method comprising the steps of:
   positioning a micro-manipulator probe near the particle, the probe having a tip;
   attaching the particle to the probe tip;
   moving the probe and the attached particle away from the first sample surface;
   removing the particle from the probe tip to a second sample surface; and,
   analyzing the composition of the particle on the second sample surface; where the second sample surface has a controlled background signal during analysis relative to the background signal of the first surface.

2. The method of claim 1 carried out in an atmosphere.

3. The method of claim 1 carried out in a vacuum.

4. The method of claim 1 where the particle is attached, moved, and removed while being irradiated by an electron beam.

5. The method of claim 1 where the particle is attached, moved, and removed while being irradiated by an ion beam.

6. The method of claim 1 where the particle is attached, moved, and removed while being irradiated by a photon beam.

7. The method of claim 1 where the second sample surface is a portion of the first sample surface.

8. The method of claim 1 where the step of moving the probe and the attached particle away from the first sample surface comprises:
   fixing the location of the probe;
   moving the first sample surface relative to the fixed probe, so as to separate the first sample surface from the probe and the attached particle.

9. The method of claim 1 where the second sample surface comprises material having an atomic number less than or equal to 12.

10. The method of claim 1 where the second sample surface comprises material having a background signal different than that of the signals expected to be generated by analysis of the particle.

11. The method of claim 1 where the step of attaching the particle to the probe tip comprises adjusting electrostatic forces to create an attractive force between the probe and particle.

12. The method of claim 11 where the adjustment of electrostatic forces further comprises:
   adjusting the energy of an energetic beam incident on the particle to electrostatically charge the particle, the first sample surface, and the probe tip so as to create an electrostatic attraction between the particle and the probe tip and to create an electrostatic repulsion between the first sample surface and the particle.

13. The method of claim 11 where energetic beam is an electron beam.

14. The method of claim 11 where energetic beam is an ion beam.

15. The method of claim 11 where the energetic beam comprises photons.

16. The method of claim 11 where the adjustment of electrostatic forces further comprises:
   the particle having an electrostatic charge; and,
   depositing a conductive material on the first sample surface to distribute and modify the electrostatic charge of the first sample surface at the location of the particle.

17. The method of claim 16 where the conductive material deposited on the first sample surface comprises polarizable molecules.

18. The method of claim 16 where the conductive material deposited on the first sample surface is an evaporated conductive film.

19. The method of claim 16 where the step of depositing a conductive material on the first sample surface comprises bombarding the first sample surface with a directed jet of a gas, and decomposing the gas with an energetic beam.

20. The method of claim 19 where the energetic beam is an electron beam.

21. The method of claim 19 where the energetic beam is an ion beam.

22. The method of claim 19 where the energetic beam comprises photons.

23. The method of claim 11 where the adjustment of electrostatic forces further comprises:
   rastering a energetic beam over a field of view that includes the particle;
   programming the raster scan to have a pre-determined dwell time and location, where the location includes the location of the particle, so as to impart an electrostatic charge to the particle.

24. The method of claim 23 where the energetic beam is an electron beam.

25. The method of claim 23 where the energetic beam is an ion beam.

26. The method of claim 23 where the energetic beam comprises photons.

27. The method of claim 11 where the adjustment of electrostatic forces comprises controlling the surface area of the particle exposed to the probe by applying the tip of the probe or the side of the probe to the particle to achieve attachment of the particle to the probe.

28. The method of claim 1 where the step of attaching the particle to the probe tip comprises adjusting a DC bias voltage between the probe and the first sample surface.

29. The method of claim 1 where the step of attaching the particle to the probe tip comprises grasping the particle with tweezers.

30. The method of claim 1 where the step of attaching the particle to the probe tip comprises the probe tip having an adhesive.

31. The method of claim 1 where the step of removing the particle from the probe to the second sample surface comprises adjusting a DC bias voltage between the probe and the second sample surface.

32. The method of claim 1 where the step of removing the particle from the probe to the second sample surface comprises applying a time-varying potential to the probe.

33. The method of claim 32 where the time-varying potential is a pulse.

34. The method of claim 32 where the time-varying potential is generated by rapidly switching stored negative charge from a capacitor through the probe.

35. The method of claim 32 where the time-varying potential is a sinusoidal voltage.

36. The method of claim 1 where the step of removing the particle from the probe to the second sample surface comprises adjusting electrostatic forces to create a repulsive force between the probe and the particle.

37. The method of claim 36 where the adjustment of electrostatic forces further comprises:

adjusting the energy of an energetic beam incident on the particle to electrostatically charge the particle, the second sample surface, and the probe tip, so as to create an electrostatic repulsion between the particle and the probe tip and to create an electrostatic attraction between the second sample surface and the particle.

38. The method of claim 37 where energetic beam is an electron beam.

39. The method of claim 37 where energetic beam is an ion beam.

40. The method of claim 37 where the energetic beam comprises photons.

41. The method of claim 36 where the adjustment of electrostatic forces further comprises the particle having an electrostatic charge; and, depositing a conductive material on the second sample surface to distribute and modify the charge on the second sample surface at the location of the particle.

42. The method of claim 41 where the conductive material deposited on the second sample surface comprises polarizable molecules.

43. The method of claim 41 where the conductive material deposited on the second sample surface is an evaporated conductive film.

44. The method of claim 41 where the step of depositing a conductive material on the first sample surface comprises bombarding the second sample surface with a directed jet of a gas, and decomposing the gas with an energetic beam.

45. The method of claim 44 where the energetic beam is an electron beam.

46. The method of claim 44 where the energetic beam is an ion beam.

47. The method of claim 44 where the energetic beam comprises photons.

48. The method of claim 36 where the adjustment of electrostatic forces further comprises:

rastering a energetic beam over a field of view that includes the particle;

programming the raster scan to exhibit a pre-determined dwell time and location, where the location includes the location of the particle, so as to impart an electrostatic charge to the particle.

49. The method of claim 48 where the energetic beam is an electron beam.

50. The method of claim 48 where the energetic beam is an ion beam.

51. The method of claim 48 where the energetic beam comprises photons.

52. The method of claim 1 where the second sample surface comprises an adhesive, for engaging the particle.

53. The method of claim 1 where the second sample surface has an elastic modulus low compared to the compliance of the probe and the elastic modulus of the particle.

54. The method of claim 1 where the second sample surface is insulating; the second sample surface having electrified patterns written into it; the charge of the electrified patterns being opposite to that of the particle.

55. The method of claim 1 where the second sample surface is wrinkled.

56. The method of claim 1 where the step of analyzing the composition of the particle further comprises:

irradiating the particle with an analysis beam; and, detecting emissions from the particle.

57. The method of claim 56 where the analysis beam is an electron beam.

58. The method of claim 56 where the analysis beam is an ion beam.

59. The method of claim 56 where the analysis beam comprises photons.

60. The method of claim 1 where the second sample surface is self-supporting, but is thin relative to the penetration depth of the analysis beam.

61. The method of claim 1 where the second sample surface is a porous surface.

62. The method of claim 1 where the second sample surface is thin relative to the penetration depth of the analysis beam, and the second sample surface is supported by an underlying framework.

63. The method of claim 62 where the underlying framework is a grid.

64. The method of claim 1 where the second sample surface is the probe tip; and, where the step of analyzing the composition of the particle comprises analyzing the composition of the particle on the probe tip.

65. The method of claim 64 where the probe and the attached particle are moved away from the first sample surface by holding the position of the probe fixed and moving the first sample surface away from the probe and the attached particle.

* * * * *